(12) United States Patent
Rossi

(10) Patent No.: US 9,677,077 B1
(45) Date of Patent: Jun. 13, 2017

(54) CATIONIC ACRYLAMIDE COPOLYMER TRANSFECTION REAGENTS

(71) Applicant: Nicholas A. A. Rossi, Madison, WI (US)

(72) Inventor: Nicholas A. A. Rossi, Madison, WI (US)

(73) Assignee: Mirus Bio LLC, Madison, WI (US)

( * ) Notice: Subject to any disclaimer, the term of this patent is extended or adjusted under 35 U.S.C. 154(b) by 0 days.

(21) Appl. No.: 14/212,748

(22) Filed: Mar. 14, 2014

(51) Int. Cl.
*C12N 15/63* (2006.01)

(52) U.S. Cl.
CPC .................................. *C12N 15/63* (2013.01)

(58) Field of Classification Search
CPC ..................................................... C12N 15/63
USPC .............................................. 526/303.1, 263
See application file for complete search history.

(56) References Cited

FOREIGN PATENT DOCUMENTS

JP         2010-115153        *   5/2010  ............. C12N 15/09

OTHER PUBLICATIONS

Zhou et al. (Deposition transfection technology using a DNA complex with a thermoresponsive cationic star polymer, Journal of Controlled Release 123 (2007) 239-246).*

* cited by examiner

*Primary Examiner* — Ling Choi
*Assistant Examiner* — Chun-Cheng Wang
(74) *Attorney, Agent, or Firm* — Mark K Johnson

(57) ABSTRACT

Cationic acrylamide copolymers have been designed and synthesized for highly efficient delivery of nucleic acids to cells in biological systems, specifically for in vitro cell transfection research.

4 Claims, 7 Drawing Sheets where $R_1$ = H, $CH_3$ $R_2$ = alkyl group containing 1 or more primary, secondary, or tertiary amines $R_3$ = H, $CH_3$ $R_4$ = $(CH_2)xCH_3$ where x = 0 - 17

Y = O, NH

MP3200 – $M_n$ 32,000 (100:0)
MP3201 – $M_n$ 63,000 (50:50)

MP3202 – $M_n$ 30,000 (67:33)
MP3204 – $M_n$ 25,000 (47:53)

CATIONIC ACRYLAMIDE COPOLYMER TRANSFECTION REAGENTS

FIELD OF THE INVENTION

The field of the present invention is compounds comprising cationic acrylamide copolymers and the use of such reagents for delivering nucleic acids to a cell.

BACKGROUND

The present invention relates to cationic polymer-nucleic acid compounds which have use in the delivery of nucleic acid to cells in biological systems, for instance in in vitro cell transfection research. The invention also relates to methods of making such compounds and potentially to gene therapy using such compounds.

The control of living processes is mediated through nucleic acids. Nucleic acids encode proteins which, as enzymes, hormones and other regulatory factors, carry out the processes which enable living organisms to function. Nucleic acids also encode for regulatory sequences which control the expression of proteins.

Because of its central role in living organisms, nucleic acids make an ideal therapeutic target. It is thought that many diseases could be controlled by the manipulation of nucleic acids in living organisms.

The key factor limiting therapies based on nucleic acid manipulation is the ability to deliver nucleic acids to the appropriate compartment of the cells. Nucleic acids are fragile molecules which are highly negatively charged (one negative charge per phosphate group) and which are readily cleaved by nucleases present both in extracellular fluids and intracellular compartments. As a highly charged molecule it will not cross the lipid membranes surrounding the cell, nor can it readily escape from endosomal compartments involved in the uptake of macromolecules into cells. Even RNAi molecules, although smaller in molecular weight, show significant problems of stability and uptake.

Cationic lipid formulations suffer from a number of shortcomings. The lipids used in these formulations are often toxic to cells, and their use as delivery vehicles for nucleic acid to cells can be limited by the toxicity of this component. Cationic lipid formulations are also unstable and have a relatively short shelf life. The short shelf life is at least partly due to the tendency of these formulations to aggregate. Furthermore, lipid formulations are generally expensive.

The use of cationic polymers overcomes some, but not all, of the problems associated with cationic lipid formulations. Polycationic polymers are, however, generally cytotoxic although some cationic polymers with lower toxicity have been reported. Cationic polymers are generally cheap to produce, and do not have the shelf life problems associated with cationic lipids.

Cationic polymers are very efficient at condensing nucleic acids into a small volume and at protecting nucleic acids from degradation by serum nucleases. Interaction is through an equilibrium reaction in which adjustment of the environmental conditions, (salt concentration, pH, molecular weight of each of the polymers) will affect the composition and form of the complexes.

In the formation of the toroids, the processes of condensation of nucleic acids and aggregation of particles are competing, so that these systems tend to be unstable with time and form larger aggregates. This is influenced by the charge ratio of the complexes, and can be reduced by using an excess of one of the components. Generally such complexes are, therefore, made with an excess of polymer, although similar complexes with an excess of nucleic acids also have some favorable properties.

The lack of efficiency of cationic polymer-nucleic acid delivery systems may relate to the efficiency with which they can be taken up into cells, and with which they can escape from the endosomal compartment of the cell, into the cytoplasm. For this reason there has been much research into incorporating ligands and other biologically-active molecules which recognize cell surface receptors involved in endocytosis, and into the use of molecules, such as amphipathic peptides, which can disrupt endosomal membranes.

Cationic polyamines such as polyethylenimine (PEI), poly(L-lysine), polyamidoamines, chitosan, poly(amino ester)s and polyacrylates have been widely investigated as nucleic acid delivery vehicles.

In comparison to cationic polyacrylates, which have ester linkages between the backbone and side groups, there has been less attention directed towards the development of cationic polyacrylamides. This may be due to the perception that acrylamides are less degradable under physiological conditions owing to the more stable amide bond between the side group and polymer backbone. A lack of degradability has often been cited as a possible issue with respect to toxicity and safety.

It is an object of the invention to overcome at least some of the above problems.

SUMMARY

Figure 1:
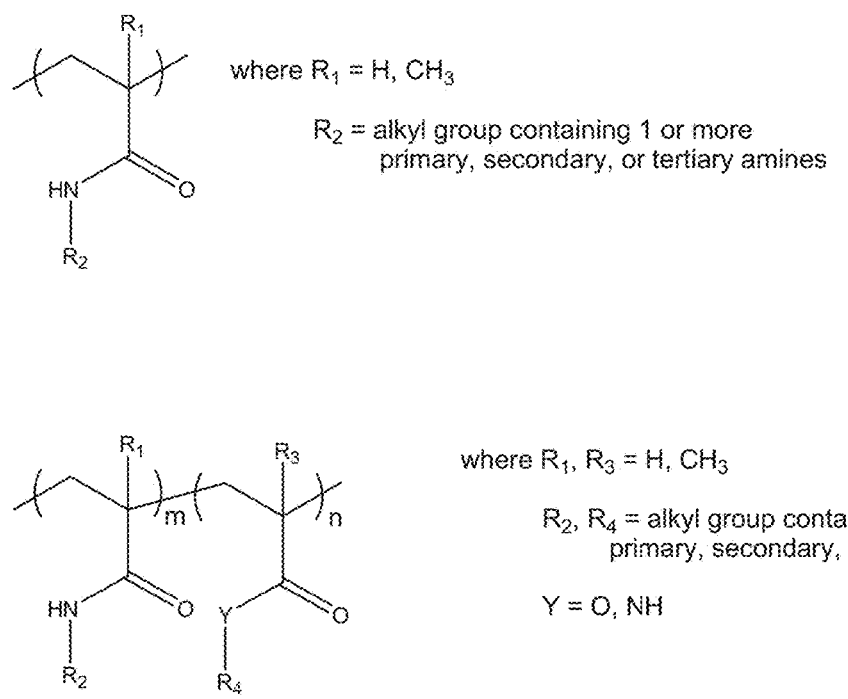
FIG. 1 shows the general structure of cationic acrylamide polymers and copolymers.

The invention pertains to the use of synthetic cationic acrylamide polymers and copolymers as nucleic acid transfection agents. In some instances, the polycations described are used in conjunction with various endosomolytic lipids to transfect nucleic acids, including RNAi, into cells.

The present invention provides a compound to assist nucleic acid transfer into animal cells via a complex comprising nucleic acid and a cationic polyacrylamide. A novel compound and method of preparation thereof, is described.

In a preferred embodiment, compositions comprising nucleic acids and cationic polyacrylamides, and processes using such compositions to deliver a nucleic acid to an animal cell in vivo or in vitro for the purposes of altering expression of a gene in the cell are described.

In a preferred embodiment, compositions and compounds are described that facilitate delivery of nucleic acid to an animal cell in vitro and in vivo. The nucleic acid comprises a double stranded structure having a nucleotide sequence substantially identical to part of an expressed target nucleic acid within the cell. Further, the use of a cationic polyacrylamide significantly increased nucleic acid transfer efficiency. The nucleic acid then alters expression of a selected endogenous nucleic acid.

In a preferred embodiment, the cationic polyacrylamide is used to assist transfection of DNA, RNA, mRNA or RNAi into a cell. The nucleic acid then alters the cell's natural process.

RNA interference (RNAi) is a phenomenon wherein double-stranded RNA, when present in a cell, inhibits expression of a gene that has an identical or nearly identical sequence. Inhibition is caused by degradation of the messenger RNA (mRNA) transcribed from the target gene. The double-stranded RNA responsible for inducing RNAi is termed interfering RNA. dsRNA introduced into the cytoplasm of a cell is first processed into RNA fragments 21-25 nucleotides long. It has been shown in in vitro studies that these dsRNAs, termed small interfering RNAs (siRNA) are generated at least in part by the RNAse III-like enzyme Dicer. Each siRNA is unwound into two single-stranded (ss) ssRNAs, the passenger strand and the guide strand. The passenger strand is degraded, and the guide strand is incorporated into the RNA-induced silencing complex (RISC). The most studied outcome is post-transcriptional gene silencing, which occurs when the guide strand base pairs with a complementary sequence in a messenger RNA molecule and induces cleavage by Argonaute, the catalytic component of the RISC complex.

RNAi has become a valuable research tool, both in cell culture and in living organisms, because synthetic dsRNA introduced into cells can selectively and robustly induce suppression of specific genes of interest. RNAi may be used for large-scale screens that systematically shut down each gene in the cell, which can help identify the components necessary for a particular cellular process or an event such as cell division. The pathway is also used as a practical tool in biotechnology and medicine. The cationic polyacrylamides described in this specification provide a mechanism to transfect siRNA and other nucleic acids into cells.

The acrylamide repeat units of the polycations described here have one or more amines present on the side chain. The amines can be either primary, secondary, or tertiary, or a combination thereof. The precursor acrylamide monomers containing primary and/or secondary amine side groups are protected with tert-butoxycarbonyl (BOC) protecting moieties. The BOC protected acrylamide monomers can be used to form homopolymers or various types of copolymers with acrylamide and/or acrylate co-monomers. The BOC groups are subsequently removed under acidic conditions post-polymerization to form the required polycations.

The development, synthesis, and characterization of cationic, acrylamide polymers are described. Various acrylamide polymers containing tertiary, secondary, and/or primary amines were synthesized using free radical polymerization. Specifically, reversible-addition fragmentation chain transfer (RAFT) polymerization was used to synthesize polyacrylamides with well defined structures, compositions, and molecular weights (Mw/Mn<1.5). Architectures include, but are not limited to, random/statistical, gradient, block, linear, branched, cross-linked/network, star, and dendritic structures. RAFT has rivaled other controlled free radical polymerization techniques such as atom transfer radical polymerization (ATRP) as one of the most effective ways to synthesize well-defined and novel polymers. The controlled synthesis of RAFT polymers is achieved using conventional radical initiators such as azobisisobutyronitrile (AIBN), and the reversible chain transfer of dithiocarbonyl compounds.

Polymers: A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft. The main chain of a polymer is composed of the atoms whose bonds are required for propagation of polymer length. The side chain of a polymer is composed of the atoms whose bonds are not required for propagation of polymer length. To those skilled in the art of polymerization, there are several categories of polymerization processes that can be utilized in the described process.

Types of Monomers: A wide variety of monomers can be used in the polymerization processes. These include positive charged organic monomers such as amines, imidine, guanidine, imine, hydroxylamine, hydrazine, heterocycles (like imidazole, pyridine, morpholine, pyrimidine, or pyrene). The amines can be pH-sensitive in that the pKa of the amine is within the physiologic range of 4 to 8. Specific amines include spermine, spermidine, N,N'-bis(2-aminoethyl)-1,3-propanediamine (AEPD), and 3,3'-diamino-N,N-25 dimethyldipropylammonium bromide. Monomers can also be hydrophobic, hydrophilic or amphipathic. Monomers can also be intercalating agents such as acridine, thiazole orange, or ethidium bromide. The polymers may have other groups that increase their utility. These groups can be incorporated into monomers prior to polymer formation or attached to the polymer after its formation. These groups include: targeting groups—such groups are used for targeting the polymer-nucleic acid complexes to specific cells or tissues.

Steric Stabilizer: A steric stabilizer is a long chain hydrophilic group that prevents aggregation of final polymer by sterically hindering particle to particle electrostatic interactions. Examples include: alkyl groups, PEG chains, polysaccharides, alkyl amines. Electrostatic interactions are the non-covalent association of two or more substances due to attractive forces between positive and negative charges.

Buffers: Buffers are made from a weak acid or weak base and their salts. Buffer solutions resist changes in pH when additional acid or base is added to the solution.

Biochemical reactions: Biological, chemical, or biochemical reactions involve the formation or cleavage of ionic and/or covalent bonds.

Reactive: A compound is reactive if it is capable of forming either an ionic or a covalent bond with another compound. The portions of reactive compounds that are capable of forming covalent bonds are referred to as reactive functional groups.

Steroid: A steroid derivative means a sterol, a sterol in which the hydroxyl moiety has been modified (for example, acylated), or a steroid hormone, or an analog thereof. The modification can include spacer groups, linkers, or reactive groups.

Sterics: Steric hindrance, or sterics, is the prevention or retardation of a chemical reaction because of neighboring groups on the same molecule.

EXAMPLES

Figure 2:
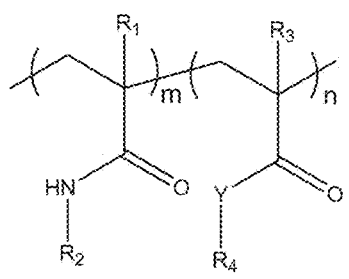
FIG. 2 shows the general structure of cationic acrylamide and alkyl acrylamide/acrylate copolymers.

Monomer synthesis: Polymers with an acrylamide or methacrylamide backbone and an alkyl side group (two or more carbons) containing one or more primary, secondary, or tertiary amines (FIG. 1). Copolymers in which at least one of the repeat units are a class of acrylamide or methacrylamide with an alkyl side group containing an amine are also described. The copolymers can be a combination of two or more different cationic repeat unit structures, or can be a combination of (meth)acrylamide and (meth)acrylate cationic units (FIG. 1). Copolymers can be a combination of (meth)acrylamide cationic units and alkyl (meth)acrylamide units, or can be a combination of (meth)acrylamide cationic units and alkyl (meth)acrylate units (FIG. 2).

Figure 3:
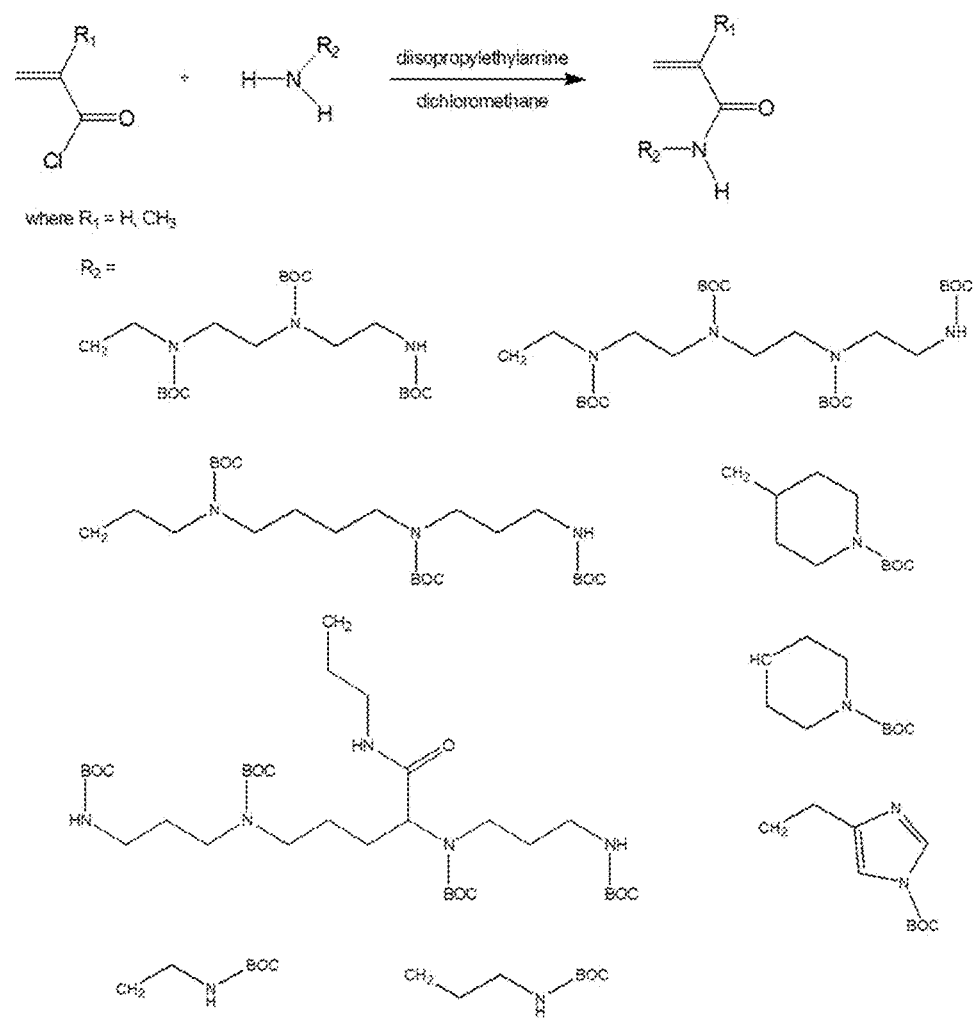
FIG. 3 shows tert-Butyloxycarbonyl (BOC) protected (meth)acrylamide monomers synthesized and polymerized by Mirus Bio LLC.
Figure 4:
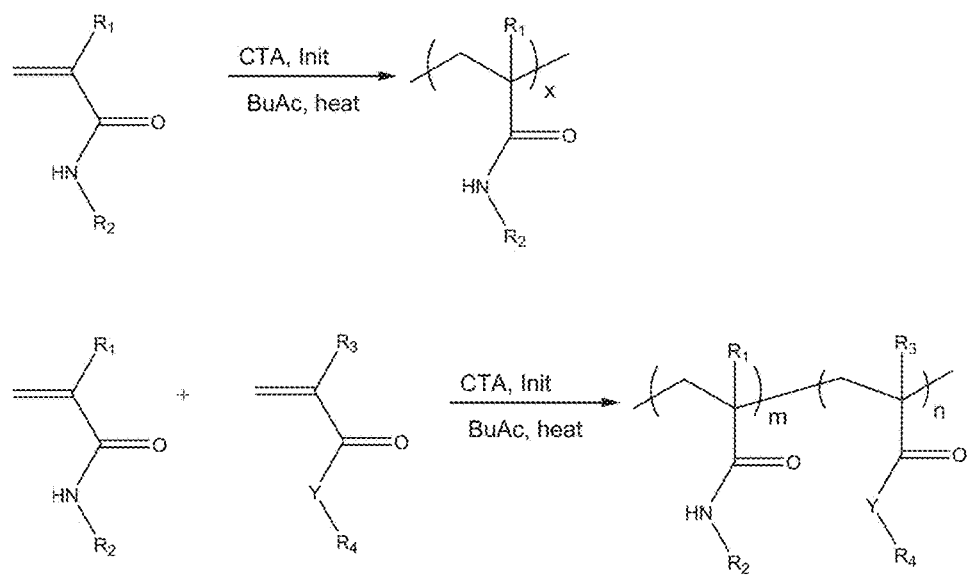
FIG. 4 shows RAFT polymerization of BOC protected (meth)acrylamide monomers in the presence of a chain transfer agent (CTA), free radical initiator (Init), solvent (butyl acetate, BuAc), and heat (60-100 C).
Figure 5:
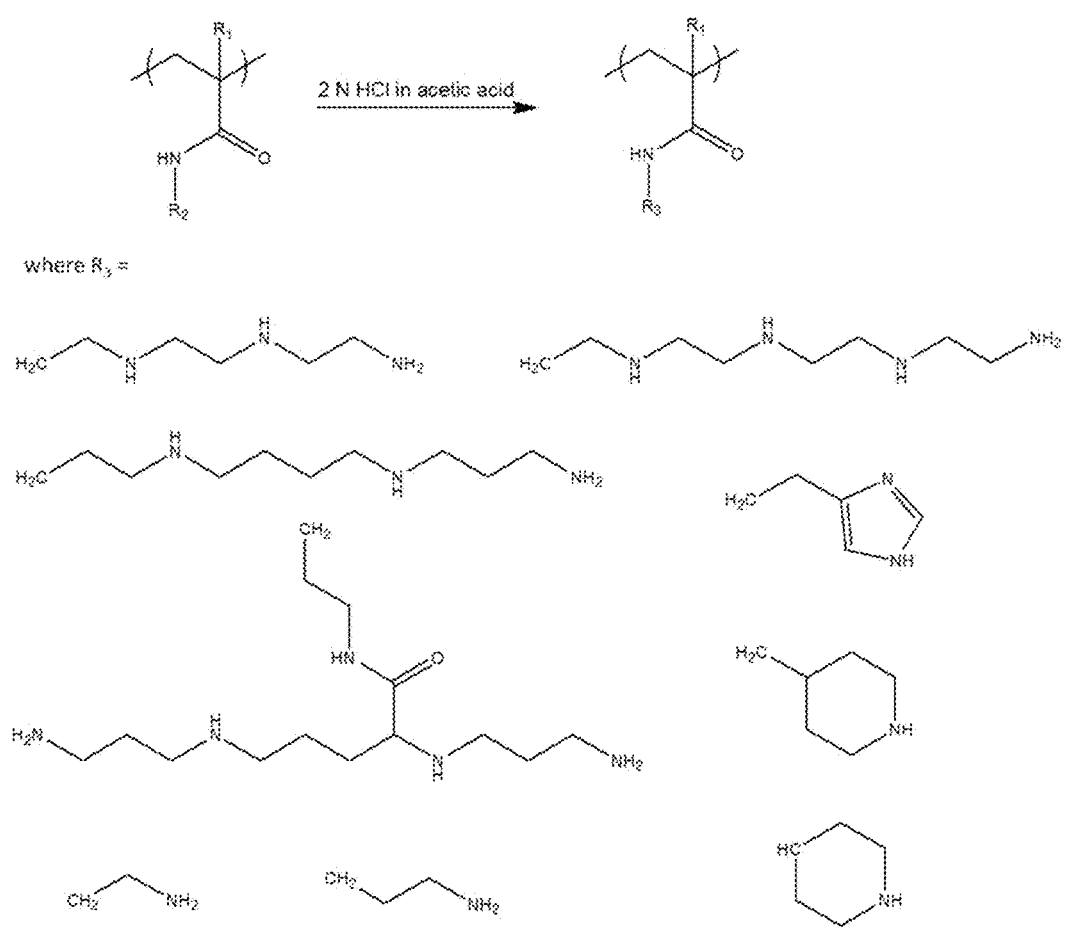
FIG. 5 shows the removal of BOC protecting groups to form cationic polymers with primary and secondary amine side chains.
Figure 6:
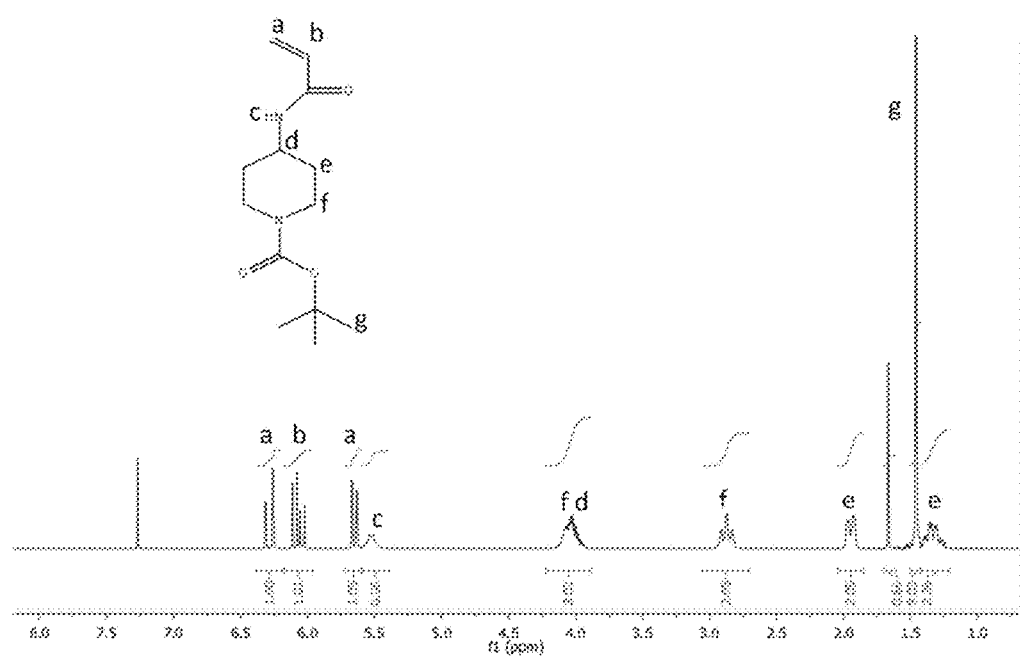
FIG. 6 shows the 1H NMR of 1-(N-BOC-piperidyl)-4-acrylamide.
Figure 7:
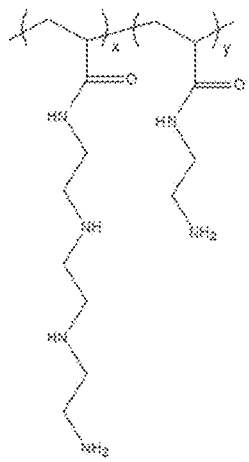
FIG. 7 shows the effects of lipids and the ratios of polymer:lipid:pDNA-reagents Transit-2020, Transit-PRO (Mirus Bio LLC, Madison, Wis.) are used as controls. Use of MC1181 lipid (Mirus Bio LLC, Madison, Wis.) at varying ratios with 4 separate polymer structures MP3200, MP3201, MP3202, and MP3204. pDNA shows greater luciferase expression compared to complexes using lipid MC1100 (Mirus Bio LLC, Madison, Wis.) at similar ratios.
Figure 7:
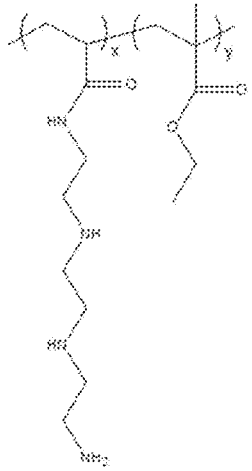
Figure 7:
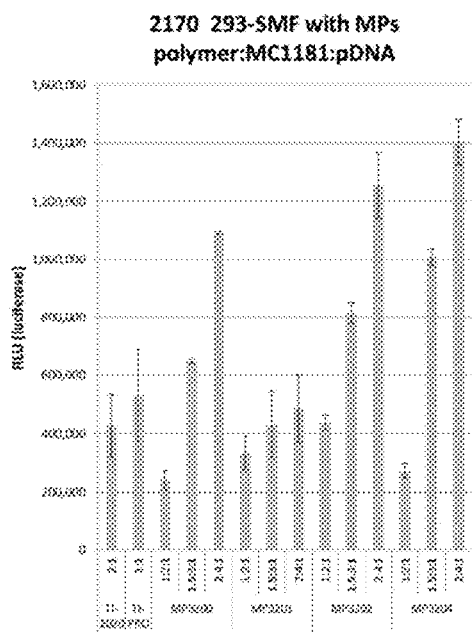
Figure 7:
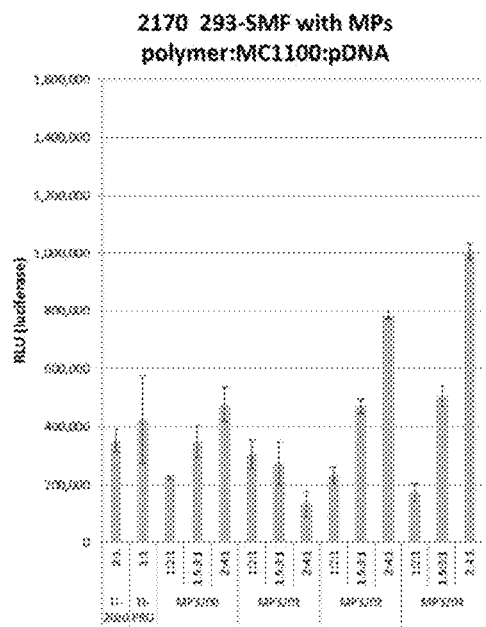

FIG. 3 highlights the tert-Butyloxycarbonyl (BOC) protected acrylamide monomers already synthesized and polymerized at Mirus Bio LLC. The monomers are synthesized by reacting acryloyl chloride or methacryloyl chloride with primary amines in the presence of a base (usually diisopropylethylamine) and solvent (usually dichloromethane). These monomers then undergo RAFT polymerization and copolymerization (FIG. 4). Once the copolymers are purified by precipitation (usually into hexane) and are analyzed by gel permeation chromatography (organic solvent phase) and $^1$H NMR (FIG. 6), they are deprotected under acidic conditions to remove the BOC protecting groups (FIG. 5).

All acrylamide monomers were synthesized based on the reaction of either acryloyl chloride or methacryloyl chloride with a primary amine containing moiety in the presence of a base (FIG. 1). The synthesis of 1-(N-BOC-piperidyl)-4-acrylamide (14PipAm) is described here as an example:

4-amino-1-boc-piperidine (5.00 g, 0.025 mol) was dissolved in dichloromethane (50 mL) and added to a dry 250 mL 3 neck round bottom flask flushed with nitrogen and equipped with a dropping funnel and stirrer bar. The flask was immersed in an ice bath before acryloyl chloride (2.47 g, 0.0272 mol) in dichloromethane (15 mL) was added to the stirring solution drop-wise via the dropping funnel over a period of 45 min. The solution was stirred overnight and allowed to warm to room temperature. The solution was washed with 10% w/v citric acid solution (20 mL), 10% potassium carbonate solution (20 mL), saturated sodium bicarbonate solution (20 mL), and brine (20 mL). The organic layer was then dried over sodium sulfate and passed through a basic alumina plug. The solvent was then removed by rotor evaporation at room temperature. The oil product was dissolved in dichloromethane (10 mL) and precipitate three times into hexane. If necessary, a silica column is also used to purify the monomer. Yield=4.0 g (63%). $^1$H NMR, δ (CDCl$_3$) ppm: 1.32 (2H), 1.45 (9H), 1.95 (2H), 2.87 (2H), 4.03 (3H), 5.52 (1H), 5.66 (1H), 6.10 (1H), 6.30 (1H).

Polymer synthesis: The monomers described were polymerized using RAFT in order to synthesize polymers of well-defined molecular weights, compositions, and architectures. The synthesis of poly(1-piperidyl)-4-acrylamide) (P14PipAm) is given as an example.

1-(N-BOC-piperidyl)-4-acrylamide (0.200 g, 0.787 mmol), 4-cyano-4(phenylcarbonothioylthio)pentanoic acid (CPCPA, 1.12 mg, 0.00401 mmol), AIBN (0.098 mg, 0.00060 mmol), and butyl acetate (1.00 mL) were added to a 20 mL glass vial with stirrer bar. The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and precipitated into hexane. The product was re-dissolved in dichloromethane and precipitated into hexane dried under reduced pressure for several hours. Yield=0.181 mg (90%). $^1$H NMR, δ (CDCl$_3$) ppm: 1.4 (9H), 1.8 (3H), 2.2 (2H), 2.8 (2H), 3.8 (2H), 4.0 (3H).

The BOC protected polyaminoacrylamides were deprotected post-polymerization to yield primary and secondary amines in the polymer side groups. The deprotection of P14PipAm-BOC is described as an example.

P14PipAm-BOC (0.150 g) was dissolved in a 2 N HCl solution of acetic acidic (4 mL) and stirred for 1 h. Water (15 mL) was added to the solution, which was then dialyzed against salt water and then deionized water over a period of 48 h. The dialyzed solution was then frozen and lyophilized to dryness (Yield=0.080 g).

TABLE 1

| | Polymer Nomenclature | $R_1$ | $R_3$ | Structure of side chains Structure |
|---|---|---|---|---|
| 1 | PEtAAm | H | Ethylamine | $CH_2$—$NH_2$ |
| 2 | PPrAAm | H | Propylamine | $CH_2$—$NH_2$ |
| 3 | PtriElAm | H | Triethylamine | $H_2C$—NH—NH—$NH_2$ |
| 4 | PtetElAm | H | Tetraethylamine | $H_2C$—NH—NH—NH—$NH_2$ |
| 5 | PSpmA | H | Spermine | $H_2C$—NH—NH—NH—$NH_2$ |

TABLE 1-continued

Structure of side chains

| Polymer | Nomenclature | $R_1$ | $R_3$ | Structure |
|---|---|---|---|---|
| 6 | PSpmPrAm | H | Spermine-carboxamide propyl? | 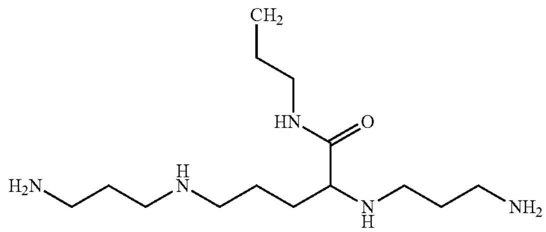 [SMILES: CCCNC(=O)C(CCCNCCCN)NCCCN] |
| 7 | PPipAm | H | 1,4-piperidine | 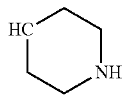 |
| 8 | PPipMeAm | H | 1-piperidyl-4-methyl | 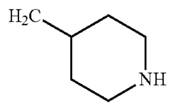 |
| 9 | PPipMAm | CH$_3$ | 1,4-piperidine | 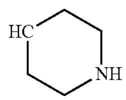 |
| 10 | PHistAm | H | histamine | 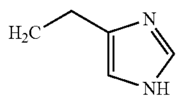 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

I claim:

1. A transfection composition comprising: a cationic polyacrylamide compound having primary or secondary amines or both for transfecting nucleic acids into cells.

2. The composition of claim 1 wherein the compound has a structure comprising:

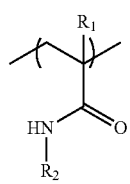

a. wherein R1 is selected from the group consisting of a hydrogen molecule and a methyl group; and,
b. R2 is selected from a group containing an alkyl group consisting of at least one primary, secondary, or tertiary amine.

3. The composition of claim 1 wherein the compound has a structure comprising:

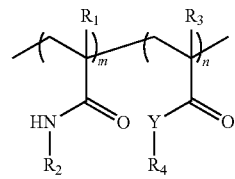

a. wherein R1 and R3 are selected from the group consisting of a hydrogen and a methyl;
b. R2 and R4 are selected from alkyl group containing at least one primary, secondary, or tertiary amine; and,
c. Y is selected from the group consisting of oxygen and NH.

4. The composition of claim 1 wherein the compound has a structure comprising:

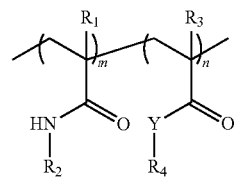

a. wherein R1 and R3 are selected from the group consisting of a hydrogen molecule and a methyl;
b. R2 is selected from the group consisting of an alkyl group containing at least one primary, secondary, or tertiary amine;
c. R4 consists of (CH2)xCH3 where x=0-17; and, d. Y is selected from the group consisting of oxygen and NH.

* * * * *